United States Patent [19]
Huntington et al.

[11] Patent Number: 5,736,580
[45] Date of Patent: Apr. 7, 1998

[54] COMPOSITION, DEVICE, AND METHOD FOR ELECTROTRANSPORT AGENT DELIVERY

[75] Inventors: James A. Huntington, Chicago; Michel Cormier, Mountain View, both of Calif.

[73] Assignee: Alza Croporation, Palo Alto, Calif.

[21] Appl. No.: 338,924

[22] Filed: Nov. 14, 1994

[51] Int. Cl.$^6$ .................................................. A61K 31/08
[52] U.S. Cl. .................................................. 514/772
[58] Field of Search .................................................. 514/772

[56] References Cited

U.S. PATENT DOCUMENTS

| | | | |
|---|---|---|---|
| 4,605,670 | 8/1986 | Kenichiro et al. | 514/619 |
| 4,722,720 | 2/1988 | Sanderson et al. | 604/20 |
| 5,023,085 | 6/1991 | Francoeur et al. | 424/449 |
| 5,084,241 | 1/1992 | Mathiesen et al. | 604/128 |
| 5,087,242 | 2/1992 | Petelenz et al. | 603/20 |
| 5,128,376 | 7/1992 | Saito et al. | 514/772 |
| 5,158,537 | 10/1992 | Haak et al. | 604/20 |
| 5,310,404 | 5/1994 | Gyory et al. | 604/20 |

FOREIGN PATENT DOCUMENTS

| | | |
|---|---|---|
| 0552879A1 | 1/1993 | European Pat. Off. . |
| 552879 | 7/1993 | European Pat. Off. . |
| WO8900853 | 2/1989 | WIPO . |
| WO9008547 | 8/1990 | WIPO . |
| WO9116930 | 11/1991 | WIPO .................. A61K 47/10 |
| WO9207618 | 5/1992 | WIPO . |

OTHER PUBLICATIONS

Database WPI, Section Ch, Week 9408, Derwent Publications Ltd., London, GB; p. P34, AN 94–061979 & JP, A, 06 016 538 (Japan Tobacco Inc.) see abstract.

Wong et al., Pharmaceutical Research, vol. 6, No. 4, 1989, "New Alkyl N,N–Dialkyl–Substituted Amino Acetates as Transdermal Penetration Enhancers".

Wong et al., Internation Journal of Pharmaceutics, vol. 52, (1989), pp. 191–202, "Unsaturated cyclic urea s new nontoxic biodegradable transdermal penetration enhancers. II. Evaluation Study".

Wong et al., Journal of Pharmaceutical Sciences, vol. 77, No. 11, Nov. 1988, pp. 967–971, Unsaturated cyclic Ureas as New Nontoxic Biodegradable Transdermal Penetration Enhancers I: Synthesis.

Pfister, William R., et al., Pharmaceutical Technology, Oct. 1990, pp. 54–60, "Permeation Enhancers Compatible with Transdermal Drug Delivery Systems: Part II: System Design Considerations".

Rolf et al. (Sep. 1988) Pharmaceutical Technology, pp. 130–140, "Chemical and Physical Methods of Enhancing Transdermal Drug Delivery".

Cullander, (1992) Advanced Drug Delivery Reviews, 9: 119–135, "What are the pathways of iontophoretic current flow through mammalian skin?".

Barry, (1987), Journal of Controlled Release, 6: 85–97, "Mode of Action of Penetration Enhancers in Human Skin".

Del Terzo, et al., Pharmaceutical Research, vol. 6, No. 1, (1989), "Iontophoretic Transport of a Honologous Series of Ionized and Nonionized Model Compounds: Influence of Hydrophobicity and Mechanistic Interpretation".

Hirvonen, et al., Proceed. Intern. Symp. Control. Rel. Bioact. Mater., 19 (1992), Controlled Release society Inc., "Transdermal Permeation of Model Anions and Cations; Effect of SkinCharge, Iontophoresis and Penetration Enhancers".

Behl, et al., Journal of Pharmaceutical Sciences, vol. 78, No. 5, pp. 355–360 (1989), "Iontophoretic Drug Delivery: Effects of Physicochemical Factors on the Skin Uptake of Nonpeptide Drugs".

Kontturi, et al., Pharmaceutical Research, vol. 10, No. 3, 1993, pp. 381–385, "Electrochemical characterization of Human Skin by Impedance Spectroscopy: The Effect of Penetration enhancers".

Yu, et al., Drug Development and Industrial Pharmacy, 17 (14),pp. 1905–1930 (1991), "Transdermal dual–Controlled delivery of Testosterone and Estradiol: (II) Enhanced Skin Permeability and Membrane–Moderated Delivery".

Chandrashekar, et al., Indian Journal of Pharmaceutical Sciences, 1994, 56(6), pp. 205–209, "Optimization of Parameters for Transdermal Permeation of Insulin".

Hcaplus 115: 239573 (1991), Yun et al.

*Primary Examiner*—Zohreh Fay
*Attorney, Agent, or Firm*—Christopher P. Rogers; D. Bryon Miller; Steven F. Stone

[57] ABSTRACT

An electrotransport drug-containing composition is provided. The composition includes a drug to be delivered through a body surface (eg, skin) of a patient, and a permeation enhancer which is solid or semisolid at temperatures typically encountered during storage of pharmaceuticals (eg, temperatures up to at least about 25° C.). The composition of the invention may be applied from a device 10 suitable for electrotransport delivery. A method for increasing electrotransport agent delivery rate and reducing body surface resistance relies on applying the composition of the invention to the body surface, and applying an electric current through the composition and the body surface.

6 Claims, 1 Drawing Sheet

COMPOSITION, DEVICE, AND METHOD FOR ELECTROTRANSPORT AGENT DELIVERY

BACKGROUND OF THE INVENTION

1. Technical Field

This invention relates generally to permeation enhancers for agent delivery by electrotransport through a body surface. More particularly, this invention relates to a composition utilizing a permeation enhancer which is solid at temperatures encountered during manufacture and/or storage of the composition, the composition being useful in electrotransport delivery devices.

2. Background Art

In the field of drug delivery, increasing efforts have been devoted to developing devices and methods which reduce patient discomfort. Some of these efforts have focused on methods for controlled, continuous drug delivery, which provide more uniform drug concentrations to the body over time. Transdermal drug delivery offers substantial improvements over traditional delivery methods. Transdermal agent delivery, as used herein, is broadly the delivery of an agent through a body surface, such as the skin, mucosa, or nails.

One type of transdermal agent delivery is electrotransport, ie, electrically assisted transdermal delivery. "Electrotransport" refers generally to the passage of a substance through a body substrate, such as skin, mucous membranes, or nails, at least partially induced by the passage of an electrical current. For example, a therapeutic agent may be introduced into the human body by electrotransport. One widely used electrotransport process, iontophoresis, involves the electrically induced transport of charged ions. Electroosmosis, another type of electrotransport, involves the movement of a liquid through a biological membrane (eg, skin) under the influence of an electric field. Another type of electrotransport, electroporation, involves the transport of an agent through transiently-existing pores formed in a biological membrane under the influence of an electric field. In any given electrotransport process, however, more than one of these processes may be occurring simultaneously to a certain extent. Accordingly, the term "electrotransport" is used herein in its broadest possible interpretation so that it includes the electrically induced or enhanced transport of an agent, which may be charged or uncharged, or a mixture thereof, regardless of the specific mechanism(s) of transport.

A common goal in the design of transdermal drug delivery devices and the selection of delivery compositions is increasing the rate of delivery of an agent to the body. The skin functions as a primary barrier to the penetration of external substances into the body and represents a major resistance to the transdermal transport of drugs into the systemic circulation. Hence, serious efforts have been focused on reducing this resistance or enhancing the permeability of the skin to the delivery of therapeutic agents.

Various methods for increasing the rate of diffusional transdermal drug delivery have been disclosed in the art. For example, drug-impermeable backing layers, made of metal, plastic, or other materials, have been employed in skin patches in order to limit diffusion of drug away from the skin and, thereby, increase the diffusion of drug into the skin. In addition, an increased rate of absorption of an agent into the skin has been produced by adjusting the temperature and relative humidity of the adjacent atmosphere. Chemical absorption promoters or permeation enhancers have also been utilized, either as integral components of a transdermal therapeutic composition or applied to the skin prior to the therapeutic agent. For example, a composition for the passive delivery of salicylic acid, which comprises aliphatic diols, an ester of a mono- or polyhydric alcohol, and a saturated fatty acid is disclosed in WO 90/08547. Another composition containing an aliphatic 1,2-diol such as propane- or butane-diol, and a fatty oil, such as triglycerides and their fatty acid derivatives, is disclosed in WO 89/00853. In addition, U.S. Pat. Nos. 4,605,670 and 5,128,376 disclose the passive percutaneous administration of an active agent in a composition containing a mixture of 1) an ester of a $C_7$–$C_{18}$ aliphatic acid and an alcohol, a $C_8$–$C_{26}$ aliphatic monoalcohol or mixtures thereof,
2) $C_4$–$C_6$ cyclic amides such as pyrrolidones, and
3) diols, triols, or mixtures thereof.

The latter compounds are said to increase the rate of percutaneous absorption of the agent. These passive methods, however, have generally proven of limited effectiveness in significantly increasing the amount of agent delivered, particularly in the case of ionizable agents.

In order to overcome the limited transdermal drug fluxes inherent in passive (ie, diffusional) transdermal delivery, electrically-assisted transdermal transport of drugs has been utilized. Electrotransport devices typically require at least two electrodes, both being in electrical contact with some portion of the skin, nails, mucous membranes, or other membrane surface of the body. One electrode, commonly referred to as the "donor" or "active" electrode, is the electrode from which the agent, drug or drug precursor is delivered into the body. The other electrode, typically termed the "counter" or "return" electrode, serves to close the electrical circuit through the body. For example, if the agent to be delivered is positively charged, ie, a cation, then the anode will be the active or donor electrode, while the cathode serves to complete the circuit. Alternatively, if the agent is negatively charged, ie, an anion, the cathode will be the donor electrode. Additionally, both the anode and cathode may be used to deliver drugs if uncharged/neutrally charged drugs are to be delivered or if both anionic and cationic drug are to be delivered. Thus, a complete electrical circuit is formed by electrical contact of the power source to the donor electrode, the donor electrode to the body, the body to the counter electrode, and the counter electrode to the power source. Furthermore, electrotransport delivery systems generally require at least one reservoir or source of the agent or drug to be delivered to the body. Examples of such agent reservoirs include a pouch or cavity, a porous sponge or pad, and a pre-formed gel body. Such agent reservoirs are electrically connected to the anode or cathode of an electrotransport device to provide a fixed or renewable source of one or more agents or drugs. In addition, electrotransport delivery systems typically have an independent electrical power source, eg, one or more batteries, and many have an electrical controller designed to regulate the flow of electric current through the electrodes and, thereby, the rate of drug delivery. The donor and counter electrodes are connected to opposite poles of the power source. Alternately, the necessary power may be supplied, at least in part, by a galvanic couple formed by the contact of two electrodes made of dissimilar materials.

Skin permeation enhancers have been utilized in transdermal electrotransport drug delivery. See for example Sanderson et al, U.S. Pat. No. 4,722,726 and Francoeur et al, U.S. Pat. No. 5,023,085. European Patent Application 93/300198.4 discloses iontophoretic transdermal delivery of agents with the aid of a broadly described group of "lipid modifiers". The modifiers are generally described as having a $C_5$–$C_{28}$ aliphatic chain and moieties such as hemiacetals, amides, acetals, alcohols, carboxylic acids, esters, and others, but containing no more than 50–60 carbon atoms. Several dioxolanes, an aliphatic carbonate, and a pyrrolidone are exemplified.

The practical utility of electrotransport permeation enhancers is generally limited by the occurrence of adverse interactions between the enhancer and the drug, between the enhancer and the body surface, or between the enhancer and the device components. (see, "Permeation Enhancers Compatible with Transdermal Drug Delivery Systems: Part II: System Design Considerations", Pharm. Tech., pp. 54–60 (October 1990). The use of a liquid permeation enhancer in an electrotransport device intended to have a shelf-life of several months or longer can present potential problems. For example, the complexity of the manufacturing process increases when liquids must be incorporated ab initio into the delivery device. Also, some liquid organic enhancers, such as ethanol or others, may dissolve, or react with, adhesive components utilized in the assembly of the delivery device. Liquid enhancers may also reduce the shelf-life of a device as a result of interactions resulting from its being in long-term contact with the drug, with polymers present in the reservoirs, or with materials utilized in its insulating portions. Further, liquids tend to promote the corrosion of metallic components (eg, electrical components, circuit traces, the electrodes, etc) in electrotransport devices.

Therefore, there is still a need for solid permeation enhancers, especially those which may be provided in a dry, solid state, in electrotransport delivery devices.

DISCLOSURE OF THE INVENTION

This invention relates to a composition that increases the electrotransport flux of an agent through a body surface without having a substantial adverse impact on the components of the device utilized. The composition of the invention is preferably provided in dry, hydratable form and, therefore, avoids certain complications in the production of electrotransport devices, as well as any damage to adhesives, metallic components, electrical components, polymeric components and other parts of the devices, which are generally troublesome with liquid permeation enhancers. One composition comprises an agent to be delivered through a body surface, such as a drug, prodrug, or the like, and a permeation enhancer which is solid or semisolid at temperatures normally encountered during manufacture and/or storage of pharmaceuticals (eg, the enhancer is in an solid or semisolid state at temperatures up to about 25° C., preferably up to about 35° C., and most preferably up to about 50° C.). Preferably, the agent and the permeation enhancer are contained in a donor reservoir of an electrotransport delivery device. Most preferably, the reservoir is substantially non-hydrated until the time of use.

The enhancer of the present invention is capable of increasing the electrotransport delivery rate of the agent through the surface. One preferred class of permeation enhancers comprise $C_{10}$–$C_{12}$ aliphatic alcohols, such as dodecane diols. Of these, 1,2-dodecane diol is most preferred. Another preferred class of permeation enhancers include dodecyl pyridinium salts, N,N-dimethyldodecylamine, octyl-N,N-dimethyldodecylamino salts, and 1-methyl-4-imidazoline-2-one-3-propylene dodecanoate.

Another preferred class of permeation enhancers has the chemical formula:

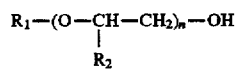

wherein n is an integer from 2 to 200;

$R_1$ is a $C_4$–$C_{18}$ saturated or unsaturated, cyclic or linear alkyl; and $R_2$ is H or $CH_3$.

Another preferred class of permeation enhancers has the chemical formula:

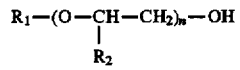

wherein n is an integer from 2 to 200 and preferably an integer from 10 to 100;

$R_1$ is a $C_4$–$C_{18}$ saturated or unsaturated, cyclic or linear alkyl and preferably a $C_8$–$C_{14}$ saturated or unsaturated, cyclic or linear alkyl; and $R_2$ is H or $CH_3$.

Another preferred class of permeation enhancers has the chemical formula:

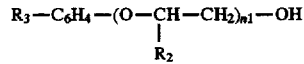

wherein $R_3$ is a saturated $C_8$–$C_9$ hydrocarbon;

n1 is an integer from 1 to 50; and $R_2$ is H or $CH_3$.

The present invention is particularly well suited for increasing the rate of electrotransport delivery of an agent through a body surface. This is achieved by placing a reservoir containing the agent and a permeation enhancer of the invention, which reservoir is hydrated at least at the time immediately prior to use, in agent and enhancer transmitting relation with a body surface (eg, skin) and applying an electrical current through the reservoir and the body surface.

MODES FOR CARRYING OUT THE INVENTION

Figure 1:
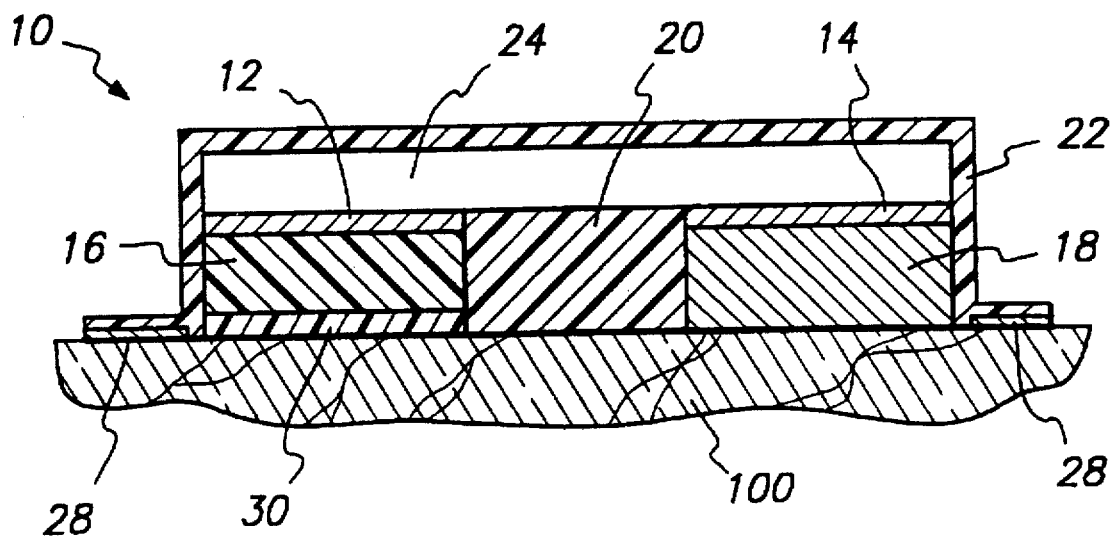
FIG. 1 shows a sectional view of one embodiment of an electrotransport device useful with the composition of the present invention.

This invention provides an electrotransportable beneficial agent-containing composition including a therapeutic beneficial agent and a permeation enhancer. In accordance with one embodiment of the invention, the permeation enhancer is solid or semisolid at temperatures normally encountered in manufacturing and/or storing pharmaceuticals, eg, at temperatures up to about 25° C., more preferably at temperatures up to at least about 35° C., and most preferably at temperatures up to at least about 50° C., which permits their remaining in solid form in the event that the temperature of the composition, or the electrotransport device containing the composition, reaches high temperatures during manufacture, shipping, handling, and/or storage. The composition is preferably contained in a donor reservoir of an electrotransport device. The reservoir may be in the form of a polymeric matrix containing the composition. More preferably, the reservoir is a substantially non-hydrated matrix which is hydrated immediately prior to use. In this manner, the advantages of electrically induced transport, with the flux enhancement of a permeation enhancer, are combined in a composition and device enjoying prolonged shelf life, while eliminating the detrimental characteristics (eg, increased corrosion and/or adverse interactions with other device components (eg, adhesives) with the attendant decreased shelf life) of liquid permeation enhancers and electrotransport devices containing them.

The term "semisolid" as used herein is intended to include permeation enhancers which are waxy at the specified temperature ranges. The solid/semisolid permeation enhancers used in this embodiment of the present invention have an additional advantage in that they are more easily added to the reservoir matrix of an electrotransport delivery device (eg, by a dry blending operation) during the manufacture of such devices compared to liquid permeation enhancers. Most problems and costs related to the containment, metering and reactivity of liquid permeation enhancers are reduced or eliminated by using the present solid/semisolid permeation enhancers. The incorporation of solid/semisolid permeation enhancers as substitutes for liquid enhancers reduces or eliminates most problems arising as a consequence of their extended contact with adhesives such as silicone adhesives, and other components of electrotransport devices. Preferably, the permeation enhancers of this invention are at least partially soluble in aqueous solutions at device operating temperatures, ie, about 20° to 40° C. The desired solubility will depend on the specific enhancer's characteristics, with the preferred water solubility of the permeation enhancer being greater than about one millimolar (mM) at about 20° C. However, in some instances solubilities substantially lower than this may suffice to provide enough concentration of the enhancer to achieve the desired flux enhancement.

One group of preferred solid electrotransport permeation enhancers comprises alcohols, diols, or other organic species having at least one hydroxyl group, including mono- and polyhydroxy alcohols, salts thereof, and mixtures thereof. A more preferred class of permeation enhancers are mono- and polyaliphatic alcohols, such as diols. Amongst these, still more preferred are $C_{10}$–$C_{12}$ aliphatic alcohols, such as dodecane diols, and more preferably 1,2-dodecane diol. The melting point of 1,2-dodecane diol is about 58°–60° C., while its water solubility at about 20° C. is greater than about 25 mM.

Another group of preferred solid electrotransport permeation enhancers comprises amines, mono- and di-substituted open and cyclic aliphatic, heterocyclic and aryl amino, salts thereof, and mixtures thereof. Amongst the N-containing enhancers, preferred are N,N-disubstituted aliphatic and heterocyclic amino compounds and their salts, and still more preferred are those having a $C_{10}$–$C_{12}$ aliphatic residue, such as dodecyl pyridinium (DDPD) salts, N,N-dimethyldodecylamine (DMDDA), N,N-dimethyldodecylamino salts, such as the acetate salt (ODAA) and 1-methyl-4-imidazoline-2-one-3-propylene dodecanoate (A3), among others.

The permeation enhancers of the present invention may be incorporated into the hydratable matrix of the donor and/or counter reservoirs of such devices in solid form at room temperature. This allows maintenance of the matrix in a substantially liquid-free state during storage and handling. Alternatively, the permeation enhancer may be incorporated into the hydrating liquid which is added to the dry state reservoir just prior to use of the device. In either case, the permeation enhancer in liquid form does not contact device components such as metallic electrodes and silicone adhesives until just prior to use of the device.

In accordance with another embodiment of the invention, the permeation enhancer is a compound selected from the following groups of compounds, some of which are liquid at temperatures of 25° to 50° C. One group of preferred permeation enhancers has the chemical formula:

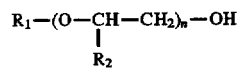

wherein n is an integer from 2 to 200 and preferably an integer from 10 to 100;

$R_1$ is a $C_4$–$C_{18}$ saturated or unsaturated, cyclic or linear alkyl and preferably a $C_8$–$C_{14}$ saturated or unsaturated, cyclic or linear alkyl; and $R_2$ is H or $CH_3$.

Some of the permeation enhancers in this group are liquid and others are solid. However, all are suitable for use herein. Examples of these permeation enhancers include Laureth-4, or Brij-30 (ICI Americas, Inc., Wilmington, Del.), and Oleth-2 or Brij-92 (ICI Americas, Inc., Wilmington, Del.), and PPG-4-Laureth-2 (Huls America, Piscataway, N.J.), among others.

Another preferred group of permeation enhancers has the chemical formula:

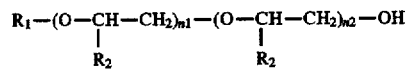

wherein n1 is an integer from 1 to 50, and more preferably an integer from 10 to 50;

the sum of (n1+n2) is an integer from 2 to 200, and more preferably an integer from 15 to 100;

$R_1$ is a saturated or unsaturated $C_4$–$C_{18}$ hydrocarbon, and more preferably a $C_8$–$C_{14}$ hydrocarbon; and $R_2$ is H or $CH_3$.

Examples of these permeation enhancers include PPG 4-Laureth 5, Marlox MO 154 (Huls America, Piscataway, N.J.), among others.

Another preferred group of permeation enhancers has the chemical formula:

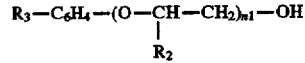

wherein $R_3$ is a saturated $C_8$–$C_9$ hydrocarbon;

n1 is an integer from 1 to 50; and $R_2$ is H or $CH_3$.

Examples of these permeation enhancers include Nonoxynol-9, and Tergitol NP-9, (Union Carbide, Tarreytown, N.Y.), among others.

The preferred concentration of permeation enhancer in a fully hydrated reservoir of an electrotransport device will depend upon the specific agent to be delivered, the size of the agent transmitting surface of the device, and the amount of electrical current applied by the device, among other things. Generally, the concentration of permeation enhancer in the hydrated donor reservoir is preferably less than about 100 millimolar (mM). More preferably, the concentration is about 1 mM to about 50 mM.

In the preferred embodiment, an increase in agent delivery rate and a decrease in body surface electrical resistance is achieved by applying an electrical potential across the body surface while simultaneously contacting the body surface with the agent to be delivered and the permeation enhancing composition. However, the body surface may be pretreated with the permeation enhancing composition. Alternatively, electrotransport delivery of the agent through the body surface may be initiated prior to contact of the body surface with the permeation enhancing composition.

This invention finds use in the electrotransport delivery of drugs and prodrugs within a broad class of compounds deliverable through body surfaces and membranes, including skin, mucosa and nails. As used herein, the expressions "beneficial agent", "therapeutic agent" and "drug" are used interchangeably and are intended to have their broadest interpretation as any therapeutically active substance which is delivered to a living organism to produce a desired, beneficial effect. "Prodrugs" are, in the present context, molecules that are converted to useful drugs or agents in vivo. In general, this includes therapeutic agents in all of the major therapeutic areas including, but not limited to, anti-infectives such as antibiotics and antiviral agents; analgesics such as fentanyl, sufentanil, and buprenorphine, and analgesic combinations; anesthetics; anorexics; antiarthritics; antiasthmatic agents such as terbutaline; anticonvulsants; antidepressants; antidiabetics agents; antidiarrheals; antihistamines; anti-inflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics including gastrointestinal and urinary; anticholinergics; sympathomimetics; xanthine derivatives; cardiovascular preparations including calcium channel blockers such as nifedipine; beta-agonists such as dobutamine and ritodrine; beta blockers; antiarrythmics; antihypertensives such as atenolol; ACE inhibitors such as ranitidine; diuretics; vasodilators including general, coronary, peripheral and cerebral; central nervous systems stimulants; cough and cold preparations; decongestants; diagnostics; hormones such as parathyroid hormones; hypnotics; immunosuppressives; muscle relaxants; parasympatholytics; parasympathomimetics; prostaglandins; proteins; peptides; psychostimulants; sedatives and tranquilizers.

More specifically, this invention is useful in the electrotransport delivery of baclofen, beclomethasone, betamethasone, buspirone, cromolyn sodium, diltiazem, doxazosin, droperidol, encainide, fentanyl, hydrocortisone, indomethacin, ketoprofen, lidocaine, methotrexate, metoclopramide, miconazole, midazolam, nicardipine, piroxicam, prazosin, scopolamine, sufentanil, terbutaline, testosterone, tetracaine, and verapamil.

The invention is particularly useful in the electrotransport delivery of peptides, polypeptides, proteins, or other macromolecules. These macromolecular substances typically have a molecular weight of at least about 300 daltons, and more typically, a molecular weight in the range of about 300 to 40,000 daltons. Examples of peptides and proteins which may be delivered using the device of the present invention include, without limitation, LHRH, LHRH analogues such as buserelin, gonadorelin, naphrelin and leuprolide, GHRH, GHRF, insulin, insulinotropin, heparin, calcitonin, octreotide, endorphin, TRH, N-36 (chemical name: N-[[(s)-4-ox-2-azetidinyl]carbonyl]-L-histidyl-L-prolinamide], liprecin, pituitary hormones (eg, HGH, HMG, HCG, desmopressin acetate), follicle luteoids, α-ANF, growth factor releasing factor (GFRF), β-MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirulog, hyaluronidase, interferon, interleukin-2, menotropins (urofollitropin (FSH) and LH), oxytocin, streptokinase, tissue plasminogen activator, urokinase, vasopressin, desmopressin, ACTH analogues, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogues, alpha-1 antitrypsin (recombinant), and TGF-beta.

The use of a solid or semisolid permeation enhancer is especially advantageous in electrotransport devices which are manufactured, shipped, and stored in a "dry" state. During use, the donor and counter reservoirs of an electrotransport device contain liquid solutions or suspensions of drug (donor reservoir) and/or electrolyte (counter reservoir). The preferred liquid solvent for the drug and the electrolyte is water due to its excellent biocompatability. Dry state electrotransport devices have donor and counter reservoirs which are substantially non-hydrated until just before use. Thus, the term "dry state" when used in connection with an electrotransport device most preferably refers to an electrotransport device having negligible water (eg, less than 10 wt % water in the reservoir) present in the donor and/or counter reservoirs after the device is assembled but before reservoir hydration. Addition of water to activate a dry state electrotransport device may occur just prior to application of the device to a body surface. Dry state electrotransport systems which contain a solid or semisolid permeation enhancer avoid processing, shelf life, and adhesive interactions problems which occur when a liquid permeation enhancer is incorporated into the reservoir(s) of an electrotransport device at the time of manufacture. Examples of dry state electrotransport devices are described in WO 92/07618 published May 14, 1992; Haak et al, U.S. Pat. No. 5,158,537; Gyory et al, U.S. Pat. No. 5,310,404; Mathieson et al, U.S. Pat. No. 5,087,241; and Petelenz, U.S. Pat. No. 5,087,242, the disclosures of which are incorporated herein by reference. The Haak device has an electrode provided with a non-hydrated matrix and a mechanism for hydrating it. The Gyory device has dry donor and electrolyte reservoirs, sealed, liquid containing pouches for both electrodes, and a mechanism for tearing the pouches and hydrating the contents of the reservoirs. In one embodiment the pouches are torn open by a tab upon removal of the device from its package, and in another the pouches are moved through a compression zone to rupture them and release their contents into the reservoirs. The Mathiesen electrode has an absorbent pad and radially oriented slits for injecting a solution. The Petelenz electrode includes a hydratable absorbing material formed of a supporting matrix and a hydratable polymer. The polymer may be hydrated with a desired liquid solution or suspension (eg, a drug-containing solution or suspension in the case of a donor reservoir or a salt solution in the case of a counter reservoir) by adding the solution or suspension thereto.

One example of an electrotransport agent delivery device which can be used to practice the present invention is illustrated in FIG. 1. Device 10 has two current conducting members, referred to herein as a donor electrode 12 and a counter electrode 14. The electrodes 12 and 14 may be composed of an electrically conductive material such as a metal. For example, the electrodes 12 and 14 may be formed from metal foil, metal screen, metal deposited or painted on a suitable backing, such as by calendering, or film evaporation, or by mixing a metal powder in a binder matrix. Examples of suitable metals include silver, zinc, silver chloride, aluminum, platinum, stainless steel, gold, and titanium. Preferably, the anodic electrode is comprised of silver, while the cathodic electrode is comprised of silver chloride. Silver is preferred over other metals because silver ions produced by the oxidation of the silver anode ($Ag \rightarrow Ag^+ + e^-$), have relatively low toxicity to humans. Silver chloride is preferred as a cathode, because the reduction of silver chloride produces chloride ions ($AgCl + e^- \rightarrow Ag + Cl^-$), which are endogenous to the human body. Alternatively, the electrodes 12 and 14 may be formed of a polymer matrix containing a conductive filler such as a metal powder, powdered graphite, carbon fibers, or other electrically conductive filler material. The polymer-based electrodes may be produced by mixing the conductive filler, eg, silver or silver chloride, in a polymer matrix.

The donor and counter electrodes 12 and 14 are positioned adjacent to the donor reservoir 16 and the counter reservoir 18, respectively. The donor reservoir 16 and optional counter reservoir 18 may be comprised of any material adapted to absorb and hold a sufficient quantity of liquid therein in order to permit transport of agent therethrough by electrotransport. For example, gauze, pads or sponges composed of cotton or other absorbent fabric, both natural and synthetic, may be used. More preferably, the matrices of the reservoirs 16 and 18 are composed, at least in part, of hydrophilic polymer material. Hydrophilic polymer is typically preferred because water is the preferred ion transport medium, and hydrophilic polymers have a relatively high equilibrium water content. More preferably, the matrices of the reservoirs 16 and 18 are solid polymer matrices composed, at least in part, of insoluble hydrophilic polymer. Insoluble hydrophilic polymer matrices are preferred for structural reasons over soluble hydrophilic polymers.

The matrices can be cross-linked with the agent components in place such as a silastic matrix, or the polymers can be prefabricated and sorbed with the components from solutions as is the case with cellulose, woven fiber pads and sponges. The agent reservoirs 16 and 18 can alternately be a gel matrix structure, formed similarly to the polymeric matrix structure, wherein the gel is formed of a hydrophilic polymer which is swellable or soluble in water. Such polymers can be blended with the components in any ratio, but preferably represent from a few percent up to about 50 percent by weight of the reservoir. The polymers can be linear or cross-linked. Suitable hydrophilic polymers include co-polyesters such as HYTREL® (DuPont De Nemours & Co., Wilmington, Del.), polyvinylpyrrolidones, polyvinyl alcohol, polyethylene oxides such as POLYOX (Union Carbide Corp.), CARBOPOL® (B F Goodrich of Akron, OH), blends of polyoxyethylene or polyethylene glycols with polyacrylic acid such as POLYOX® blended with CARBOPOL®, polyacrylamide, KLUCEL®, cross-linked dextran such as SEPHADEX® (Pharmacia Fine Chemicals, AB, Uppsala, Sweden), WATER LOCK® (Grain Processing Corp., Muscatine, Iowa) which is a starch-graft-poly(sodium acrylate-co-acrylamide) polymer, cellulose derivatives such as hydroxyethyl cellulose, hydroxypropylmethylcellulose, low-substituted hydroxypropylcellulose, and cross-linked Na-carboxymethylcellulose such as Ac-Di-Sol® (FMC Corp., Philadelphia, Pa.), hydrogels such as polyhydroxylethyl methacrylate (National Patent Development Corp.), natural gums, chitosan, pectin, starch, guar gum, locust bean gum, and the like, along with blends thereof. Of these, polyvinylpyrrolidones are preferred. This list is merely exemplary of the materials suited for use in this invention. Other suitable hydrophilic polymers can be found in J. R. Scott & W. J. Roff, Handbook of Common Polymers (CRC Press, 1971), which is hereby incorporated by reference.

The matrices of the reservoirs 16 and 18 may also optionally contain a hydrophobic polymer for enhanced structural rigidity. Preferably the hydrophobic polymer is heat fusible, in order to improve the lamination of the reservoirs 16 and 18 to adjacent components, such as the insulator 20 shown in FIG. 1. Suitable hydrophobic polymers for use in the reservoir matrices include, but are not limited to, polyisobutylenes, polyethylene, polypropylene, polyisoprenes and polyalkenes, rubbers, copolymers such as KRATON®, polyvinylacetate, ethylene vinyl acetate copolymers, polyamides such as nylons, polyurethanes, polyvinylchloride, acrylic or methacrylic resins such as polymers of esters of acrylic or methacrylic acid with alcohols such as n-butanol, 1-methyl pentanol, 2-methyl pentanol, 3-methyl pentanol, 2-ethyl butanol, isooctanol, n-decanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, itaconic acid, N-branched alkyl maleamic acids wherein the alkyl group has 10–24 carbon atoms, glycol diacrylates, and blends thereof. Most of the above-mentioned hydrophobic polymers are heat fusible. Of these, polyisobutylenes are preferred.

The reservoir matrices may be a polymeric matrix structure formed by blending the desired agent, drug, electrolyte, permeation enhancer, or other component(s), with an inert polymer by such processes as melt blending, solvent casting, or extrusion. Typically, the donor reservoir 16 contains a drug to be delivered, while the counter reservoir 18 contains an electrolyte, eg, a water soluble biocompatible salt. In addition to the drug and electrolyte, the reservoirs 16 and 18 may also contain other conventional materials such as dyes, pigments, inert fillers, and the like. The counter reservoir 18 may contain one or more biocompatible electrolytic salts, such as sodium chloride.

An insulating member 20 separates the donor electrode 12 and donor reservoir 16 from the counter electrode 18 and counter reservoir 18. The insulator 20 prevents direct ion transport, ie, short circuiting, between the donor reservoir 16 or the donor electrode 12 and the counter electrode 14 or counter reservoir 18. Insulator 20 is made of material impermeable to the passage of water, ions, and electrons. Preferably, the insulating material is a material capable of strong bonding with the reservoir polymers, thereby providing further overall structural integrity for the device. Preferred insulating materials include polyisobutylenes and ethylene vinyl acetates.

The device 10 also has a backing layer 22 composed of a waterproof, and preferably electrically insulating material. In addition, the backing layer 22 may provide some structural integrity to the device.

Electrical power is supplied to electrodes 12 and 14 by a power generating circuit, shown schematically in FIG. 1 as layer 24. Circuit layer 24 may include one or more batteries, and optionally include current controlling circuitry. Circuit 24 is in electrical contact with the electrodes 12 and 14 such that each electrode is in electrical contact with the opposite pole of the power source in circuit 24. Although some power may be provided by a galvanic couple between the electrodes, an independent electrical power source in circuit 24 is a preferred means of powering the electrotransport device. The circuit 24 may include one or more batteries, connected in series or in parallel, and positioned between the counter electrode 14 and donor electrode 12. One or more 3 volt button cell batteries, such as PANASONIC® model CR 2025, are suitable to power electrotransport devices.

The circuit 24 may include electronic circuitry for controlling the operation of the electrotransport device for example, circuitry permitting the patient to manually turn the system on and off, such as with an on-demand medication regime, or to turn the system on and off with some desired periodicity, for example, to match the natural or circadian patterns of the body. A relatively simple controller or microprocessor can control the current as a function of time or can generate complex current wave forms such as pulses or sinusoidal waves. The control circuitry may also include a biosensor and some type of feedback system which monitors biosignals, provides an assessment of therapy, and adjusts the drug delivery accordingly. A typical example is the monitoring of the blood sugar level for controlled administration of insulin.

The device 10 adheres to the body surface 100 by means of a peripheral adhesive layer 28. Other conventional means for maintaining device 10 in contact with body surface 100 (eg, straps, adhesive overlays, in-line adhesives, etc) may also be used.

An optional passive flux control membrane 30 is positioned between donor reservoir 16 and the body surface 100 for controlling passive agent delivery (ie, flux under no applied electrical potential).

The device 10 of FIG. 1 is merely one example of an electrotransport agent delivery device useful in accordance with present invention. In addition, the system may contain other features, such as a removable protective liner (not shown) on the skin contacting face of the device. Furthermore, certain components in device 10 are unnecessary or optional. Counter reservoir 18 is one example of an optional component. Also, if electrodes 12 and 14 are chosen such that a galvanic couple exists, an independent power source (eg, a battery) in circuit 24 may be an optional component. Further, the permeation enhancing composition of this invention is useful in multicomponent devices. For example, the electrodes may be attached to separate body surface locations and connected by external wiring. There are numerous other electrotransport device or system configurations known in the art and contemplated useful with the present invention.

Having thus generally described the invention, the following examples will illustrate how variations of the above-described parameters provide therapeutically effective electrotransport systems.

EXAMPLES

Preparation of Human Cadaver Skin Samples

Human cadaver skin was prepared by first removing about 1 mm thick skin samples with an electric dermatome in the form of strips. The skin strips were placed in polyethylene bags, sealed and placed in a refrigerator at about 4° C. for temporary storage. Prior to use in the electrotransport cell, the skin strips were placed in one-liter beakers containing water at 60° C. for about 90 seconds with gentle stirring. Then, the skin strips were removed and placed onto the absorbent side of a piece of BENCHKOTE™ fabric with the dermis side down. Using flat tipped tweezers to retain the dermis, the epidermis was removed from each strip with a round-tip spatula. Each epidermis, stratum corneum side up, was transferred to a PYREX™ glass tray which was filled with water. Each floating epidermis was stretched essentially flat. After removal from the water 2.22 cm (⅞ in.) diameter disks of each epidermis were punched out of areas having negligible surface damage. The disks were stored at 4° C. in a sealed container with water droplets to maintain their moisture.

Set-up of Electrotransport Cell and Composition

Figure 2:
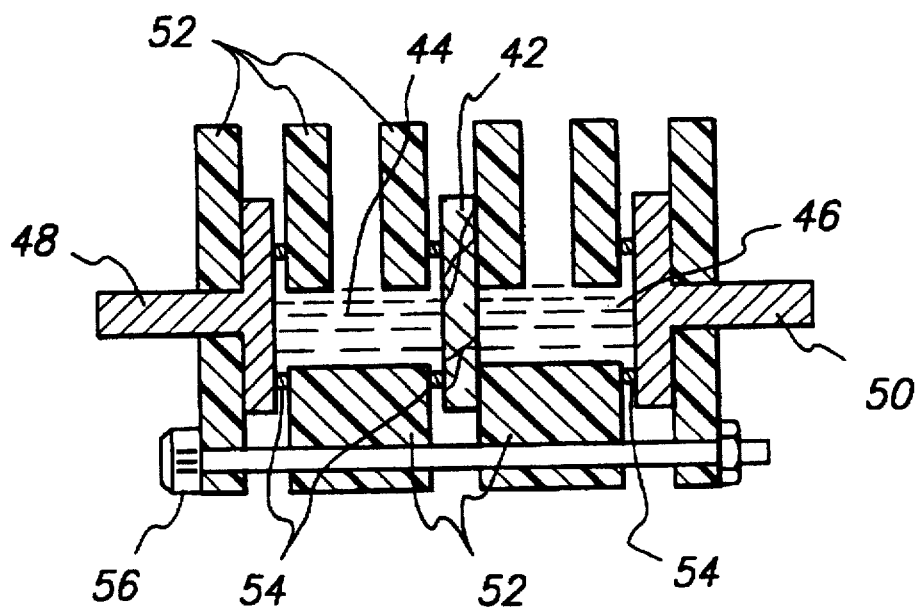
FIG. 2 shows a sectional view of a two compartment cell used for in vitro testing of electrotransport drug flux in the presence of various permeation enhancers.

The human cadaver epidermis disks were mounted between compartments 44 and 46 of the electrotransport permeation cell shown in FIG. 2. The cell was comprised of a polycarbonate support structure 52, including O-ring seals 54, and the assembly was held together with stainless steel bolt and nut 56. The human skin disk 42 separated the anodic compartment 44 and the cathodic compartment 46. A silver anode 48 was placed adjacent to the anodic compartment 44, and a silver chloride cathode 50 was placed adjacent to the cathodic compartment 46. The area of the human skin disk 42 exposed for transport was about 1.26 cm$^2$ and the volume of each of compartments 44 and 46 was about 2 ml. The electrodes 48, 50 were electrically connected to a galvanostat (not shown in FIG. 2), which can be set to apply the voltage necessary to achieve a constant predetermined level of electric current. The galvanostat was set to apply a current of 126 µA, ie, 100 µA/cm$^2$ across electrodes 48, 50 throughout each test.

Example 1

A solution of sodium ketoprofen, initially at a concentration of about 100 mg/ml, and each selected permeation enhancer were successively placed in the cathodic donor compartment 46. Dulbecco's phosphate buffered saline (about 0.15M NaCl with minor amounts of other ions, pH 7.0) was placed in the anodic receptor compartment 44. The skin resistance was calculated from the voltages applied by the galvanostat according to Ohm's law, ie, $R_{skin}=\Delta V/i$, where $\Delta V$ is the potential applied by the galvanostat, and i is the applied current, 126 microamps. The ketoprofen flux was determined by periodical sampling of the solution in the receptor compartment 44.

The system was maintained at about 32° C. by a Haake Model D1 heating block/water bath. The cell voltage was monitored over the entire procedure, and then averaged. The skin resistance was calculated from Ohm's law as described above using the measured $\Delta V$.

The samples were automatically taken from the receptor compartment every one to two hours, except for overnight experimentation, with an Isco Model 2230 autosampler and a metering pump. Receptor samples were taken and the ketoprofen concentrations determined via high performance liquid chromatography using a Shimadzu Model SCL-6B chromatograph, while the voltage measurements were taken to determine the skin resistance. Each run was conduced in triplicate, including the control, to minimize error. All cells were set up with tissue from the same cadaver. The selected permeation enhancer was placed in the donor compartment, while the control cell's donor compartment contained no enhancer.

Generally, the flux and voltage remained at a steady state after about 4 hrs. The steady state flux values obtained and the skin resistances calculated are shown in Table 1 below in normalized form, ie, all values were divided by the appropriate control value obtained in the absence of enhancer. Thus, the flux control and the skin conductivity control were each assigned a value of 1, and the flux/conductivity values obtained after addition of each permeation enhancer to the donor solution are normalized to the control. Thus, a flux value of 1.99 means that ketoprofen flux was 1.99 times the flux measured in the control. Similarly, a skin conductivity (skin conductivity is the inverse of skin resistance or $1/R_{skin}=i/\Delta V$) value of 5.69 means that the electrical conductivity of the skin disk was 5.69 times that of the skin disk in the control.

The permeation enhancers utilized in these tests included dodecanol/ethanol, 1,2-dodecane diol, 1,2-dodecane diol/ethanol, octyl-N,N-dimethyl-dodecylamino acetate (ODAA)/ethanol, 1-methyl-4-imidazoline-2-one-3-propylenedodecanoate (A3)/ethanol, N,N-dimethyl-dodecylamine (DMDDA), and dodecyl-pyridinium chloride (DDPDCI). The weight ratio of permeation enhancer to ketoprofen in the reservoir composition was about 1 to 10. Since the flux of ketoprofen is pH dependent, with the optimum at about 6, the pH of the DMDDA solution was adjusted down to 7.20 from 9.20 by addition of 140 ml of 0.5M HCl. The skin conductivity and ketoprofen flux values obtained are reported in Table 1 normalized with respect to control, ie, flux and conductivity values obtained in the absence of enhancer.

TABLE 1

Enhancement of Electrotransport of Ketoprofen by Permeation Enhancers

| Permeation Enhancer | pH | Normalized Ketoprofen Flux (after 5 hrs) | Normalized Skin Conductivity (after 5 hrs) |
|---|---|---|---|
| Control (no enhancer) | 6.70 | 1.00 | 1.00 |
| 25 mM Dodecanol in 20% Ethanol | 7.05 | 4.88 | 34.7 |
| 25 mM 1,2-Dodecanediol | 6.90 | 1.99 | 5.69 |
| 25 mM 1,2-Dodecanediol in 20% Ethanol | 7.05 | 1.95 | 6.81 |
| 10 mM ODAA in 20% Ethanol | 7.30 | 1.56 | 4.61 |
| 10 mM A3 in 20% Ethanol | 7.00 | 1.76 | 5.93 |
| 10 mM DMDDA | 7.20 | 1.37 | 2.71 |
| 10 mM DDPDCI | 6.90 | 1.06 | 1.58 |

Table 1 above illustrates the effectiveness of various electrotransport enhancers in increasing electrotransport delivery rates and electrical skin conductivity, ie, reducing skin resistivity. The greatest enhancement was found with dodecanol. 1,2 dodecanol was observed to be effective for enhancing both flux and skin conductivity in the presence and in the absence of ethanol. The presence of ethanol, as solvent for 1,2-dodecane diol, did not affect ketoprofen flux, but skin conductivity increased by about 20%. The enhancement of skin conductivity produced by 1,2-dodecane diol alone without ethanol was more than double that of the other permeation enhancers. The ketoprofen flux was enhanced by addition of 1,2-dodecane diol to about double the control value. Other permeation enhancers, without ethanol, yielded increases in ketoprofen flux of 6% and 37%. The ketoprofen flux was enhanced by the addition of dodecanol and ethanol to almost 5 times the control value. Other permeation enhancers, with ethanol, yielded increases in ketoprofen flux of 56%, 76% and 95%.

Having thus generally described the invention and certain preferred embodiments thereof, it will be readily apparent that various modifications to the invention may be made by workers skilled in the art without departing from the scope of this invention, which is limited only by the following claims.

We claim:

1. A method of increasing electrotransport flux of an agent through a body surface comprising:

contacting a body surface with a hydrated reservoir containing a beneficial agent to be delivered through the body surface and a permeation enhancer in an amount which is effective to increase the electrotransport of the agent, and applying an electric current across the reservoir and the body surface whereby the agent fluxes across the body surface at an enhanced flux compared with the flux in the absence of the enhancer, said permeation enhancer being selected from the group consisting of i) and ii) wherein i) is selected from the group consisting of dodecanol, 1,2-dodecane diol, octyl-N,N,-dimethyldodecylamino salts, 1-methyl-4-imidazoline-2-one-3-propylenedodecanoate, N,N-dimethyldodecylamine, a dodecylpyridinium salt, and mixtures thereof, and ii) is compounds having the chemical formula:

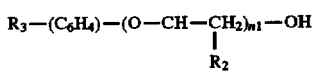

wherein $R_3$ is a saturated $C_8$–$C_9$ hydrocarbon;

n1 is an integer from 1 to 50; and $R_2$ is H or $CH_3$.

2. The method of claim 1, wherein the permeation enhancer is a solid or semisolid at temperatures up to at least about 25° C.

3. The method of claim 1, wherein the hydrated reservoir further contains ethanol.

4. The method of claim 1, wherein the permeation enhancer is selected from the group consisting of dodecanol, 1,2-dodecane diol, octyl-N,N,-dimethyldodecylamino salts, 1-methyl-4-imidazoline-2-one-3-propylenedodecanoate, N,N-dimethyldodecylamine, a dodecylpyridinium salt, and mixtures thereof.

5. The method of claim 1, wherein the permeation enhancer comprises dodecanol.

6. The method of claim 1, wherein the permeation enhancer comprises 1,2-dodecanediol.

* * * * *